(12) United States Patent
Parks

(10) Patent No.: US 7,071,228 B2
(45) Date of Patent: Jul. 4, 2006

(54) METHOD OF TREATING MUSCULOSKELETAL AND CONNECTIVE TISSUE INFLAMMATIONS

(76) Inventor: L. Dean Parks, 2420 SE. 15th St., Ocala, FL (US) 34471

( * ) Notice: Subject to any disclaimer, the term of this patent is extended or adjusted under 35 U.S.C. 154(b) by 0 days.

(21) Appl. No.: 10/278,706

(22) Filed: Oct. 23, 2002

(65) Prior Publication Data
US 2004/0082655 A1    Apr. 29, 2004

(51) Int. Cl.
*A01N 37/00*    (2006.01)
*A61K 31/19*    (2006.01)

(52) U.S. Cl. .................. 514/557; 568/378; 568/447; 568/668; 568/824; 514/859; 424/451; 424/464; 424/489

(58) Field of Classification Search ............. 514/559, 514/825, 962, 557; 424/451, 464, 489; 568/378, 568/447, 668, 824
See application file for complete search history.

(56) References Cited

U.S. PATENT DOCUMENTS 5,457,129 A * 10/1995 Aggarwal et al. .......... 514/557

OTHER PUBLICATIONS

Cousins et al., Ceruloplasmin and Metallothionein Induction by Zinc and 13-Cis Retinoic-Acid in Rats with Adjuvant Inflammation, Proc Soc Exp Biol Med, (1985) 179(2), 168-172. See: abstract.*

Brinckerhoff et al., Inflammation and Collagenase Production in Rats With Adjuvant Arthritis Reduced With 13-Cis-Retinoic Acid, Science (WASH DC), (1983) 221 (4612), 756-458. See: abstract.*

Bottomley et al., Acute Achilles Tendon Following Oral Isotretinoin Therapy for Acne Vulgaris, Clinical Experimental Dermatology, 1992, vol. 17, No. 4, pp. 250-251, abstract.*

The Physicians Desk Reference, Electronic Edition, ACCUTANE® (Roche Laboratories), (isotretinoin), capsules.*

Webster's Ninth New Collegiate Dictionary, Merriam-Webster Inc. Publishers, 1984, p. 1011.*

Osteoarthritis or Rheumatoid Arthritis? Know the Difference. http://www.ra.com/ra/rastore/cgi-bin/PrintFriendly-Cat-200156 MavRoot 303 ProdID 200630htm.

Arthritis and Auto-Immune Disease. http://www.askdoctrish.com/arthritis.htm.

Clinical pharmacokinetics 1985 Jan.-Feb.;10(1) 38-62, Lucek RW, Clinical pharmacokinetics of the retinoids, http://www.ncbl.nim.nih.gov/entrez query.fcgi.

Cancer Research (Jul. 17, 1995);Retinoid-induced suppression of squamous cell differentation in human oral squamous cell crcinoma xenografts (line 1483) in athymic nude mice.

Biochem Pharmacol. May 15, 2003;65(10):1685-90., Gagnon I, et al. Enzymatic Characterization of recombinant mousa retinal dehydrogenase type 1.

* cited by examiner

*Primary Examiner*—Christopher S. F. Low
*Assistant Examiner*—Amy Lewis
(74) *Attorney, Agent, or Firm*—M. K. Silverman; Yi Li

(57)    ABSTRACT

A method of treating said musculoskeletal and connective tissue inflammations including osteoarthritis and associated articular and periarticular inflammations, and non-articular Rheumatism including capsulitis, tendonitis, fibrositis, and perarticular inflammations is disclosed. The method includes administering to a patient of a therapeutically effective amount of a composition comprising 13-cis-retinoic acid. Preferably, the treatment method includes administering to a patient of an initial dosage of a composition comprising 13-cis-retinoic acid for an initial treatment period, and thereafter administering a maintenance dosage of the composition.

7 Claims, No Drawings

METHOD OF TREATING MUSCULOSKELETAL AND CONNECTIVE TISSUE INFLAMMATIONS

FIELD OF THE INVENTION

The present invention relates to a method for treatment of musculoskeletal and connective tissue inflammations. More specifically, the method utilizes 13 cis-retinoic acid to effectively treat musculoskeletal and connective tissue inflammations including osteoarthritis and associated articular and periarticular inflammations, and non-articular Rheumatism including capsulitis, tendonitis, fibrositis, and periarticular inflammations.

BACKGROUND OF THE INVENTION

Musculoskeletal and connective tissue inflammations are common diseases affecting a large human population. Some commonly seen musculoskeletal and connective tissue inflammations include osteoarthritis and associated articular and periarticular inflammations, and non-articular Rheumatism including capsulitis, tendonitis, fibrositis, and periarticular inflammations.

Osteoarthritis is the most common type of arthritis, especially among older people. Osteoarthritis is a joint disease that mostly affects the cartilage. Cartilage is the slippery tissue that covers the ends of bones in a joint. Healthy cartilage allows bones to glide over one another. It also absorbs energy from the shock of physical movement. In osteoarthritis, the surface layer of cartilage breaks down and wears away. This allows bones under the cartilage to rub together, causing pain, swelling, and loss of motion of the joint. Over time, the joint may lose its normal shape. Also, bone spurs may grow on the edges of the joint. Bits of bone or cartilage can break off and float inside the joint space. This causes more pain and damage. People with osteoarthritis usually have joint pain and limited movement. Unlike some other forms of arthritis, osteoarthritis only affects joints, and not internal organs.

Osteoarthritis is one of the most frequent causes of physical disability among adults. More than 20 million people in the United States probably have the disease. Some younger people get osteoarthritis from a joint injury, but osteoarthritis most often occurs in older people. In fact, by age 65, more than half of the population has x-ray evidence of osteoarthritis in at least one joint. Since the number of older Americans is increasing, so is the number of people with osteoarthritis. Both men and women have the disease.

Existing osteoarthritis treatment approaches include exercise, medicines, rest and joint care, surgery, pain relief techniques, alternative therapies, and weight control. The commonly used medicines in treating osteoarthritis include nonsteroidal anti-inflammatory drugs (NSAIDs), for example, aspirin, Advil® (ibuprofen), Motrin® IB (ibuprofen), Aleve® (naproxen sodium), ketoprofen; topical pain-relieving creams, rubs, and sprays (for example, capsaicin cream) applied directly to the skin; corticosteroids, powerful anti-inflammatory hormones made naturally in the body or man made for use as drugs, typically injected into affected joints to relieve pain temporarily; and hyaluronic acid, a new medicine for joint injection, used to treat osteoarthritis of the knee. Surgery may be performed to resurface (smooth out) bones, reposition bones, and replace joints. For some people, surgery helps relieve the pain and disability of osteoarthritis. Osteoarthritis is a chronic disease. Although various medications have been used for treating the disease, they are not effective for long term control and prevention.

One of most common forms of capsulitis is adhesive capsulitis, also referred as "frozen shoulder", a painful condition which results in a severe loss of motion in the shoulder. The symptoms are primarily pain and a reduced range of motion in the joint due to the severe inflammation of the joint capsule. The shoulder usually hurts when movement reaches the limit of the range of motion, and can be quite painful at night. The cause of this condition is not clear. One theory is that the condition may be due to an autoimmune reaction. Adhesive capsulitis may begin following other injuries where the shoulder is not moved around normally because of the other injury. A common example is after a wrist fracture the arm may be kept in a sling for several weeks, which limits the shoulder movement. In addition, the frozen shoulder condition can begin while other shoulder problems are present. Sometimes, problems such as bursitis, impingement syndrome, or a partial rotator cuff tear can lead to a frozen shoulder as well.

Usually, the adhesive capsulitis must be treated first to regain motion in the shoulder before the underlying problem can be addressed. Treatment of the frozen shoulder can be frustrating and slow. Initial treatment is directed at decreasing inflammation and increasing the range of motion of the shoulder with a stretching program. Anti-inflammatory medications can be used. It is important that a physical therapy program be started and continued to regain the loss of motion. An injection of cortisone and long-acting anesthetic may bring the inflammation under better control, and allow the stretching program to be more effective. Most cases will eventually improve, but it is common that the range of motion is not fully recovered.

Tendonitis is an inflammatory condition characterized by pain at tendinous insertions into bone. Common sites of tendonitis include rotator cuff of the shoulder (supraspinatus and bicipital tendons); insertion of the wrist extensors (lateral epicondylitis and tennis elbow) and flexors (medial epicondylitis) at the elbow; patellar and popliteal tendons and iliotibial band at the knee; insertion of the posterior tibial tendon in the leg (shin splints); and achilles tendon at the heel. Tendonitis most commonly is caused by overuse. Pathologic changes consistent with chronic inflammation usually are observed. Tissue degeneration, characterized by cell atrophy, also may be observed. Calcium can deposit along the course of the tendon (ie, calcific tendinitis), with the shoulder being the most common site. Chronic tendonitis can lead to weakening of the tendon and subsequent rupture. Middle-aged adults are most susceptible to the development of tendonitis.

The goals of pharmacotherapy in treating tendonitis are to control pain and decrease inflammation. Existing treatments include nonsteroidal anti-inflammatory drugs (NSAIDs), splinting or immobilization; and peritendinous lidocaine/corticosteroid injection. Nonsteroidal anti-inflammatory drugs include, ibuprofen, flurbiprofen, naproxen, mefenamic acid, ketoprofen, indomethacin, and piroxicam.

Fibrositis is a relatively common form of nonarticular rheumatism. Fibrositis can be localized or diffuse. The diffuse fibrositis, occurring at multiple locations of the body is also called fibromyalgia. Fibrositis and fibromyalgia are disorders associated with pain and tenderness of muscle and adjacent connective tissue, which indicate pain in fibrous tissues, muscles, tendons, ligaments, and other sites. Any fibromuscular tissues may be involved, but those of the occiput, neck, shoulders, thorax, low back and thighs are especially affected. For fibromyalgia various focal "trigger points" of tenderness can be identified, and systemic symptoms such as fatigue, insomnia, and depression are frequently present.

The pain and sore spots characteristic of fibrositis can be due to several causes. First, there may be a local inflammation due to a virus. This is like having a "cold" in your back or neck. Generalized muscle pains may be due to systemic toxins in the blood that results from a viral infection, usually somewhere else other than in the aching muscles or joint capsules. Further, one common cause of localized tender spots is what is called "referred pain". A common site of inflammation due to trauma, such as a strain or a sprain, is in the many joints in connection with the spine. Because these joints are close to the coverings of the nerves being distributed from the spinal cord, the covering of these nerves called the "dura" may become irritated or inflamed. When this happens, the trouble is not where it hurts, but deeper inside around the inflamed joint linings and nerve coverings. If the pain and tenderness last for more than a few months, then chronic pain and joint stiffness can result. The above described mechanism occurs in many different body sites. The elbow, heel, back, neck, and shoulder associated with painful tender spots are common locations. The existing treatments for fibrositis include cortisone injection, nonsteroidal anti-inflammatory drugs (NSAIDs), and physical therapies. For fibromyalgia, the treatments also include tricyclic antidepressants for relaxing muscles and improving quality of sleep, exercise and self-relaxation.

Many of the musculoskeletal and connective tissue inflammations are chronic and cause chronic regional pain and loss of functionality of affected areas. These diseases can hurt people more than physically. Their finances and lifestyles are also affected. Financial effects include the cost of treatment, and wages lost because of disability. Lifestyle effects include depression, anxiety, feelings of helplessness, limits on daily activities, job limitations, and loss of everyday family joys and responsibilities.

13-cis retinoic acid, more generally known as retinoic acid, also referred to as isotretinoin, and sold under the trademark Accutane® from Hoffmann-La Roche Inc., Nutley, N.J., has long been known as a topical and oral dermatological agent used in the treatment of acne vulgaris and several other skin diseases. 13-cis retinoic acid inhibits sebaceous gland function and keratinization. The exact mechanism of action of Accutane® in treating acne is unknown. Since retinoic acid is a teratogenic drug and, because of the mutagenic effects associated with such drugs, it is only used for treating severe acne vulgaris when other treatments are not effective.

Since 1992 there have been literature reports on the potential effect of 13-cis-retinoic acid upon human prostate cancer cells. U.S. Pat. No. 5,612,354 (to Sanz et al) discloses a method of treating mammals suffering from disorders which are characterized by an increased proliferation or abnormal differentiation of cells by the systemic or topical administration to the mammals of an effective amount of (1H-azol-1-ylmethyl) substituted quinoline derivatives, including 13-cis-retinoic acid. It is believed that because of the capability to delay the metabolism of retinoic acid, (1H-azol-1-ylmethyl) substituted quinoline derivatives may potentially be used in treating cancers.

As described above, it is apparent that there still is a strong need for medications that can effectively treat musculoskeletal and connective issue inflammations. A medication that can provide a long term control of musculoskeletal and connective tissue inflammations, inhibit further progress of existing conditions, and prevent reoccurrence of acute symptoms will have important medical significance for millions of people who suffer from these diseases.

SUMMARY OF THE INVENTION

In one embodiment, the present invention relates to a method of treating musculoskeletal and connective tissue inflammations, including osteoarthritis and associated articular and periarticular inflammations, and non-articular Rheumatism including capsulitis, tendonitis, fibrositis, and periarticular inflammations. The method comprises administering to a patient of a therapeutically effective amount of a composition comprising 13-cis-retinoic acid. The composition further comprises a pharmaceutical carrier, and the composition can be in the forms of powder, pill, capsule, tablet, and liquid. Preferably, the method of treating musculoskeletal and connective tissue inflammations, including osteoarthritis and associated articular and periarticular inflammations, and non-articular Rheumatism including capsulitis, tendonitis, fibrositis, and periarticular inflammations, comprises the steps of: administering to a patient of an initial dosage of a composition comprising 13-cis-retinoic acid for an initial treatment period; and thereafter administering a maintenance dosage of the 13-cis-retinoic acid composition.

In a further embodiment, the present invention relates to a combined method of treating osteoarthritis and associated articular and periarticular inflammations, and non-articular Rheumatism including capsulitis, tendonitis, fibrositis, and periarticular inflammations. The combined method employs a conventional method for treating musculoskeletal and connective tissue inflammations, and administration to the patient a therapeutically effective amount of composition comprising 13-cis-retinoic acid.

It is accordingly an object of the present invention to provide a medicine for treating musculoskeletal and connective tissue inflammations and related symptoms.

The above and other objectives and advantages of the present invention will become apparent from the hereinafter set forth Detailed Description of the Invention and claims appended herewith.

DETAILED DESCRIPTION OF THE INVENTION

In one embodiment, the method of the present invention is directed to a method of treating musculoskeletal and connective tissue inflammations. The suitable types of musculoskeletal and connective tissue inflammations include, but are not limited to, osteoarthritis and associated articular and periarticular inflammations, and non-articular Rheumatism including capsulitis, tendonitis, fibrositis, and periarticular inflammations. The method comprises administering to a patient of a therapeutically effective amount of a composition comprising 13-cis-retinoic acid. The therapeutically effective amount is in a range from about 10 mg to about 80 mg of 13-cis-retinoic acid of an average daily intake (about 0.14 mg to about 1.1 mg per kilogram (kg) of body weight).

The composition further comprises a pharmaceutical carrier. Common pharmaceutical carriers include liquid carriers such as water, glycols, oils, alcohols, syrups, and the like in the case of oral liquid preparations such as suspensions, syrups, elixirs and solution; and solid carriers such as starches, sugars, kaolin, lubricants, binders, disintegrating agents and the like in the case of powders, pills, capsules, and tablets; and other pharmaceutical carriers known in the art. The composition used for the purpose of the present invention can be in various forms, such as powders, pills, capsules, tablets, and liquids. Although oral administration is preferred because of its convenience, other suitable systemic administrations can also be used for the purpose of the present invention.

13-cis-retinoic acid is commercially available as a medicine under the trade name Accutane® from Hoffmann-La Roche Inc., Nutley, N.J. for treating certain dermatological diseases. Accutane® has three available doses, 10 mg, 20 mg, and 40 mg soft gelatin capsules.

Preferably, the treatment method further includes two treatment periods: an initial treatment, and a maintenance treatment. First, in the initial treatment, a patient administrates an initial dosage of 13-cis-retinoic acid for a period from about ten days to about five months. Thereafter, the patient administrates a lower maintenance dosage of 13-cis-retinoic acid.

Preferably, the initial treatment period is about two to three weeks, because beyond two to three weeks, side effects of the medicine, such as tenderness at sites of old injuries to the fibro-musculo-skeletal system, dry skin, chapped lips, dry eyes, and dry nose, tend to occur. If these side effects occur during the initial treatment period, they normally subside after the maintenance dosage is instituted. However, if a patient does not have adverse side effects, the initial treatment period can be extended accordingly to enhance the effect of the medication on the musculoskeletal and connective tissue inflammations. Based on the fact that currently 13-cis-retinoic acid is used to treat severe acne patients for a continuous period of 20 weeks, the initial treatment period of the present invention can be substantially longer than several weeks depending on the responses and conditions of individual patients.

The low maintenance dosage has two functions. First, the treatment with the maintenance dosage, after the initial treatment, needs several weeks to control existing musculoskeletal and connective tissue inflammations, and to inhibit further progress of existing inflammatory conditions. Secondly, a long term administration of the maintenance dosage can prevent reoccurrence of musculoskeletal and connective tissue inflammations which are common clinically with various chronic musculoskeletal and connective tissue inflammations. Therefore, preferably, the maintenance dosage is administered for long term.

The dosage is determined based on the patient's body weight. The initial dosage is in a range from about 10 mg to 80 mg 13-cis-retinoic acid daily (about 0.14 mg to about 1.1 mg per kilogram (kg) of body weight). For average men having a body weight about 160 lbs (72.6 kg), the average initial dosage is about 40 mg daily. The maintenance dosage is in a range from about 10 mg to 80 mg 13-cis-retinoic acid every three to seven days (about 0.14 mg to about 1.1 mg per kilogram (kg) of body weight). The average maintenance dosage for average men having a body weight about 160 lbs is about 40 mg every three to seven days. The dosages should be adjusted accordingly for children or those who weigh substantially less than or above the average body weight.

The daily dosage can be administrated in a single dose, or divided doses. Since Accutane® has three commercially available doses, 10 mg, 20 mg, and 40 mg soft gelatin capsules, for a 40 mg initially dosage, the patient can either take a 40 mg capsule, or take two 20 mg capsules daily, or take four 10 mg capsule daily. The same applies to the dosage in the maintenance treatment. For convenience, during the maintenance treatment the patients can take one 40 mg dose about every three to seven days.

It has been found that with the treatment using the method of the present invention the patients who were diagnosed with musculoskeletal and connective tissue inflammations achieved various degrees of improvements of their disease conditions. The observed improvements include reduction of pain and tenderness caused by musculoskeletal and connective tissue inflammations at various affected body locations, such as cervical spine, shoulder, hand, hip, and neck; reduction of swelling of the joints; dissolution of fibro calcified peri-spinous nodules of cervical spine; reduction of stiffness of the joints and increased range of motions; and recovery of physical abilities. Furthermore, no serious adverse side effects were observed by using the described treatment.

Based on the clinical effectiveness of the medicine, it is believed that 13-cis-retinoic acid controls musculoskeletal and connective tissue inflammations, dissolves and remodels the articular and periarticular arthritic changes caused by the diseases, including the dissolution of thickening of the ligaments and joint capsules, and dissolves osteofibrochondromatous changes in the periarticular areas and remodels the disease generated changes to a more normal architecture. The detailed mechanism of 13-cis-retinoic acid on treating musculoskeletal and connective tissue inflammations are not known.

Importantly, it has been found that with a long term use of the low maintenance dosage, 13-cis-retinoic acid provides a long term control of musculoskeletal and connective tissue inflammations, inhibits further progression of existing inflammatory conditions, and prevents reoccurrence of acute conditions of those chronic musculoskeletal and connective tissue inflammations. In view of the large population of people that have these common chronic diseases and the loss of natural body functions with advanced conditions, and lack of effective long term prevention and control, the discovery of the present invention has an important medical significance.

In a further embodiment, the method of the present invention can be used as an adjuvant to other conventional methods for treating musculoskeletal and connective tissue inflammations. The conventional methods include cortisone injection, surgical treatments, systematically administering nonsteroidal anti-inflammatory drugs, and physical therapies. Administration of an effective amount of 13-cis-retinoic acid can be used to assist other conventional treatment methods and to enhance the overall efficiency of the treatments. 13-cis-retinoic acid can be administered concurrently with the conventional methods, for example, together with cortisone or hyaluronic acid injection; conventional medications such as nonsteroidal anti-inflammatory drugs, chondrotin sulfate, and glucosamine; or physical therapies. 13-cis-retinoic acid treatment method of the present invention can also be used prior to or after surgical procedures.

Example 1 to 3 illustrate clinical effectiveness of the above described treatment method. An initial treatment and a maintenance treatment as described above were prescribed to the patients. It is noted that the patients described in the Examples were in the average weight range, therefore, an average dosage of 40 mg was used. It is noted that all patients were told to totally avoid sun exposure during the initial treatment dosage period and for the first one or two weeks after instituting the maintenance dosage because of sun sensitivity with the use of Accutane®.

EXAMPLE 1

A 62 year old white male patient in generally good health had the onset of joint complaints in 1988 affecting only the hands. The main location was in the distal interphalangeal joint (IP joint) which had been fractured in 1980. Symptoms were puffiness and swelling with increasing tenderness over the years. The tenderness had become so pronounced that in 1994 he stopped shaking hands because of the pain. In addition he had progressive difficulty making a fist because of swelling and tightness of the fingers.

X-ray examination found thining of joint space and capsular swelling of the interphalangeal joints. Laboratory examination results were normal. The patient was diagnosed with osteoarthritis with capsulitis.

Several therapeutic treatments with this patient were of minimal or no benefit. The treatments included Asprin (two to five 325 mg pills per day); Motrin™ (ibuprofen) and Naprosyn™ (naproxen); and Glucosamine/Chondroitin sulfate.

In April 1997 the patient started taking Accutane® (13-cis retanoid acid, Hoffmann-La Roche Inc., Nutley, N.J.) for another medical condition in an initial dosage of about 40 mg Accutane® daily for twenty one days, followed by a maintenance dosage of about 40 mg Accutane® twice a week (on Monday and Friday). Over the ensuing months the patient noted gradual, but steady improvement of his hand condition, and improvement of his stiff and painful shoulder condition caused by an old rotator cuff injury to the right shoulder. Furthermore, the patient also noted a slow improvement of cervical spine tenderness (which had been chronic since a severe whip lash injury in a 1968 car wreck), with increased range of motion (ROM) and dissolution of fibro calcified peri-spinous nodules of cervical spine.

Because of the apparent improvement of the patient's osteoarthritis and capsulitis conditions, the patient has continued the Accutane® treatment with the maintenance dosage described above to the present. No physical side effects have been noted other than dry lips and skin in the early stages. During the initial treatment an increased right shoulder pain was noted, which then abated. The patient's blood-chemistries and hematology test results have remained normal.

The patient's overall physical well being has improved immensely and he no longer has any musculoskeletal infirmities.

EXAMPLE 2

A 69 year old white male retired Navy Chief Warrant Officer was diagnosed with inflammatory osteoarthritis and rheumatism. The symptoms included joint pains for six to ten years. Initially in 1992 the join pains affected the right hip, and the patient suffered from the hip pain while working. In 1994, the patient developed neck and left shoulder pain. X-rays examination results showed calcification of the cervical spine. Furthermore, the shoulder was diagnosed as a rotator cuff injury. In 1997, the patient's hands became tender when playing golf. The hand condition progressed to puffiness of fingers and a gripping problem with difficulty closing hands. The patient's blood chemistry was normal.

The patient was treated in the past with Aspirin and Motrin™, which had minimal effect. The glucosamine/chondroitin treatment had only a temporary effect. Physical therapy had some relief of the hand condition. The patient worried that he could no longer play golf as often as he wanted, and was even forced to consider stopping golf, because of difficulties with swing and gripping.

The patient was placed on the 13-cis retanoic acid treatment on May 1, 2002 with an initial dosage about 40 mg Accutane® daily for fourteen days, followed by a maintenance dosage of about 40 mg Accutane® twice a week. After total of seven weeks of treatment the patient's shoulder pain completely abated (note he continued physical therapy on this area during the 13-cis retanoic acid treatment), the range of movement returned to normal. The patient's neck and hip pains almost completely abated (as of August, 2002). The patient's hands still exhibit a tinge of tenderness if he plays golf three to four days in a row. However, hand puffiness and grip problems no longer exist. As a result of such a significant improvement of the physical condition, the patient's golf handicap dropped from eleven (11) to nine (9).

The patient had minimal side effects with the 13-cis retanoic acid treatment including dry skin and lips and some initial increased pain in the left shoulder which later subsided.

EXAMPLE 3

A 61 year old white male farmer, had more than a ten year history of hand pain involving fingers, and associated with swelling and tenderness of interphalangeal joints. The hand condition made his work and playing golf difficult. The patient was diagnosed with osteoarthritis.

The patient was placed on 13-cis retanoic acid treatment in April of 2001, with an initial dosage of about 40 mg Accutane® daily for twenty one days, followed by a maintenance dosage of about 40 mg Accutane® twice a week. After ten weeks treatment, the patient's symptoms began to improve, including decreased swelling and tenderness of the fingers, and improvement of the range of movement. The improvements were maintained during a subsequent six month continuation of the maintenance dosage.

The patient's pre-therapy and follow-up blood tests were normal. The patient had no side effects other than dry lips and skin. This subsided after taking the maintenance dosage.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

What is claimed is:

1. A method of treating musculoskeletal and connective tissue inflammations comprising the steps of:
   (a) orally administering to a human having musculo skeletal and connective tissue inflammations an initial dosage of about 10 mg to about 80 mg daily of 13cis-retinoic acid for an initial treatment period, wherein said musculoskeletal and connective tissue inflammations are selected from the group consisting of osteoarthritis, articular inflammations, periarticular inflammations, non-articular Rheumatism, capsulitis, and tendonitis, and
   (b) thereafter administering a maintenance dosage of about 10 mg to about 80 mg of 13-cis-retinoic acid every three to seven days, wherein said musculoskeletal and connective tissue inflammation is reduced.

2. A method of treating musculoskeletal and connective tissue inflammations comprising the steps of:

(a) treating a human having musculoskeletal and connective tissue inflammation with a method selected from the group consisting of cortisone injection, hyaluronic acid injection, surgical treatments, systemically administering nonsteroidal anti-inflammatory drugs, physical therapies, and combinations thereof, wherein said musculoskeletal and connective tissue inflammations are selected from the group consisting of osteoarthritis, articular inflammations, periarticular inflammations, non-articular Rheumatism, capsulitis, and tendonitis, (b) orally administering to said human an initial dosage of about 10 mg to about 80 mg daily of 13cis-retinoic acid for an initial treatment period, and (c) thereafter administering a maintenance dosage of about 10 mg to about 80 mg of 13-cis-retinoic acid every three to seven days, wherein said musculoskeletal and connective tissue inflammation is reduced, wherein said musculoskeletal and connective tissue inflammation is reduced.

3. The method of claim 1, wherein said composition further comprises a pharmaceutical carrier.

4. The method of claim 3, wherein said composition is in a form selected from the group consisting of powder, pill, capsule, tablet, and liquid.

5. A method of treating musculoskeletal and connective issue inflammations comprising the steps of:

(a) treating a human having musculoskeletal and connective tissue inflammation with a method selected from the group consisting of cortisone injection, hyaluronic acid injection, surgical treatments, systemically administering nonsteroidal anti-inflammatory drugs, physical therapies, and combination thereof, wherein said musculoskeletal and connective tissue inflammations comprises osteoarthritis or associated articular or periarticular inflammations, or non-articular Rheumatism including capsulitis, tendonitis, fibrositis, or periarticular inflammations, (b) orally administering to said human an initial dosage from about 10 mg to about 80 mg daily of 13cis-retinoic acid for an initial treatment period, and (c) thereafter administering a maintenance dosage from about 10 mg to about 80 mg every three to seven days of said composition.

6. The method of claim 5, wherein said composition further comprises a pharmaceutical carrier.

7. The method of claim 6, wherein said composition is in a form selected from the group consisting of powder, pill, capsule, tablet, and liquid.

* * * * *

UNITED STATES PATENT AND TRADEMARK OFFICE
CERTIFICATE OF CORRECTION

PATENT NO. : 7,071,228 B2
APPLICATION NO. : 10/278706
DATED : July 4, 2006
INVENTOR(S) : L. Dean Parks It is certified that error appears in the above-identified patent and that said Letters Patent is hereby corrected as shown below:

Column 8, line 56, change "13cis-retinoic acid" to --13-cis-retinoic acid--

Column 8, line 60, after "capsulitis", add --fibrositis,--

Column 8, from line 66 to Column 9, line 19, change

"2. A method of treating musculoskeletal and connective tissue inflammations comprising the steps of:
(a) treating a human having musculoskeletal and connective tissue inflammation with a method selected from the group consisting of cortisone injection, hyaluronic acid injection, surgical treatments, systematically administering nonsteroidal anti-inflammatory drugs, physical therapies, and combinations thereof, wherein said musculoskeletal and connective tissue inflammations,
(b) orally administering to said human an initial dosage of about 10 mg to about 80 mg daily of 13cis-retinoic acid for an initial treatment period, and
(c) thereafter administering a maintenance dosage of about 10 mg to about 80 mg."

to

--2. The method of Claim 1, wherein said initial period is from about ten days to five months.--

Column 9, from line 25 to Column 10, line 18, change

"5. A method of treating musculoskeletal and connective issue inflammations comprising the steps of:
(a) treating a human having musculoskeletal and connective tissue inflammation with a method selected from the group consisting of cortisone injection, hyaluronic acid injection, surgical treatments, systematically administering nonsteroidal anti-inflammatory drugs, physical therapies, and combination thereof, wherein said musculoskeletal and connective tissue inflammations comprises osteoarthritis or associated articular or periarticular inflammations, or non-articular Rheumatism including capsulitis, tendonitis, fribrositis, or periarticular inflammations,
(b) orally administering to said human an initial dosage of from about 10 mg to about 80 mg daily of 13cis-retinoic acid for an initial treatment period, and
(c) thereafter administering a maintenance dosage from about 10 mg to about 80 mg every three to seven days of said composition."

to

UNITED STATES PATENT AND TRADEMARK OFFICE
CERTIFICATE OF CORRECTION

PATENT NO.       : 7,071,228 B2
APPLICATION NO. : 10/278706
DATED            : July 4, 2006
INVENTOR(S)      : L. Dean Parks It is certified that error appears in the above-identified patent and that said Letters Patent is hereby corrected as shown below:

--5. A method of treating musculoskeletal and connective tissue inflammations comprising the steps of:
(a) treating a human having musculoskeletal and connective tissue inflammation with a method selected from the group consisting of cortisone injection, hyaluronic acid injection, surgical treatmeans, systematically administering nonsteroidal anti-inflammatory drugs, physical therapies, and combinations thereof, wherein said musculoskeletal and connective tissue inflammations are selected from the group consisting of osteoarthritis, articular inflammations, periarticular inflammations, non-articular Rheumatism, capsulitis, fibrositis, and tendonitis,
(b) orally administering to said human an initial dosage of about 10 mg to about 80 mg daily of 13-cis-retinoic acid for an initial treatment period, and
(c) thereafter administering a maintenance dosage of about 10 mg to about 80 mg of 13-cis-retinoic acid every three to seven days, wherein said musculoskeletal and connective tissue inflammation is reduced.--

Signed and Sealed this

Second Day of September, 2008

JON W. DUDAS
*Director of the United States Patent and Trademark Office*